United States Patent [19]

Douglas et al.

[11] Patent Number: 5,635,200
[45] Date of Patent: Jun. 3, 1997

[54] TASTE-MAKING COMPOSITIONS OF RANITIDINE

[75] Inventors: Stephen J. Douglas; Jill Evans, both of Ware, Great Britain

[73] Assignee: Glaxo Group Limited, Greenford, Great Britain

[21] Appl. No.: 411,828

[22] PCT Filed: Oct. 14, 1993

[86] PCT No.: PCT/EP93/02832

§ 371 Date: Apr. 12, 1995

§ 102(e) Date: Apr. 12, 1995

[87] PCT Pub. No.: WO94/08576

PCT Pub. Date: Apr. 28, 1994

[30] Foreign Application Priority Data

Oct. 16, 1992 [GB] United Kingdom .................. 9221760
Oct. 16, 1992 [GB] United Kingdom .................. 9221800

[51] Int. Cl.$^6$ .................................. A61K 9/28; A61K 9/16
[52] U.S. Cl. ....................... 424/441; 424/484; 424/490; 424/497; 424/498
[58] Field of Search .............................. 424/441, 484, 424/490, 497, 498

[56] References Cited

U.S. PATENT DOCUMENTS

| | | | |
|---|---|---|---|
| 4,865,851 | 9/1989 | James et al. | 424/498 |
| 5,028,432 | 7/1991 | Chupra et al. | 414/451 |
| 5,032,393 | 7/1991 | Douglas et al. | 424/79 |
| 5,057,319 | 10/1991 | Gottwald et al. | 424/441 |
| 5,075,114 | 12/1991 | Roche | 424/470 |
| 5,084,278 | 1/1992 | Mehta | 424/441 |
| 5,085,868 | 2/1992 | Mattson et al. | 424/490 |
| 5,219,563 | 6/1993 | Douglas et al. | 424/78.1 |
| 5,260,072 | 11/1993 | Roche et al. | 424/464 |
| 5,275,823 | 1/1994 | France et al. | 424/489 |
| 5,290,569 | 3/1994 | Nagafuzi et al. | 424/490 |
| 5,320,848 | 6/1994 | Geyer et al. | 424/441 |
| 5,380,535 | 1/1995 | Geyer et al. | 424/484 |
| 5,429,825 | 7/1995 | Reo et al. | 424/490 |

FOREIGN PATENT DOCUMENTS

| | | |
|---|---|---|
| 2 068 366 | 11/1992 | Canada . |
| 0 257 368 | 3/1988 | European Pat. Off. . |
| 0 273 890 | 7/1988 | European Pat. Off. . |
| 0 322 048 | 6/1989 | European Pat. Off. . |
| 0 421 581 | 4/1991 | European Pat. Off. . |
| 2 643 263 | 8/1990 | France . |
| 2 204 792 | 11/1988 | United Kingdom . |
| 2 218 333 | 11/1989 | United Kingdom . |
| WO92/04893 | 4/1992 | WIPO . |
| WO92/21328 | 12/1992 | WIPO . |

*Primary Examiner*—Shep K. Rose
*Attorney, Agent, or Firm*—Robert H. Brink

[57] ABSTRACT

This invention relates to a composition which is substantially free of the bitter taste associated with ranitidine and comprises: a) a dispersion of lipid coated particles of ranitidine or a physiologically acceptable salt thereof in a non-aqueous vehicle; b) particles comprising ranitidine or a physiologically acceptable salt thereof incorporated into a core and coated with a lipid coating; c) lipid coated particles of a form of ranitidine which is poorly soluble in water; and processes for the preparation thereof and pharmaceutical compositions thereof.

17 Claims, No Drawings

TASTE-MAKING COMPOSITIONS OF RANITIDINE

This application is a 371 of PCT/EP93/02832 filed on Oct. 14, 1993 published as WO94/08576 Apr. 28, 1994.

The present invention relates to improvements in the formulation of the histamine $H_2$-receptor antagonist ranitidine, particularly for oral administration.

Ranitidine, N-[2-[[5-[(dimethylamino)methyl]-2-furanylmethyl]-thio]ethyl]-N'-methyl-2-nitro-1,1-ethenediamine, and its physiologically acceptable salts are described and claimed in British Patent Specification No. 1565966, and a particular crystalline form of ranitidine hydrochloride is described and claimed in British Patent Specification No. 2084580B. In both these specifications there is reference to formulations for oral administration, which may take the form of for example tablets, capsules, granules, powders, solutions, syrups, suspensions, or tablets or lozenges for buccal administration. Oral preparations of ranitidine are also disclosed in British Patent Specification Nos. 2142820, 2198352, 2218336, 2219940, 2222772 and 2229094.

Oral administration constitutes a preferred route for administering ranitidine. Ranitidine, however, in common with many drug substances, has an inherently bitter taste, and this constitutes a disadvantage with certain types of oral preparation. Moreover, it is well known that patients may not complete a necessary course of medicine if they are prescribed an oral presentation which is particularly unpleasant to taste. The problems resulting from the bitter taste of ranitidine are particularly acute in formulations such as chewable tablets, granules, powders, solutions or suspensions. To some extent, the bitter taste may be masked by the use of sweetening and/or flavouring agents, although this is not entirely satisfactory, and an unpleasant after-taste may still remain in the mouth. In addition, there may be circumstances in which it is undesirable or inappropriate to use a sweetening and/or flavouring agent.

Various methods of taste-masking ranitidine have been described. For example, British Patent Specification No. 2218333 describes complexes formed between ranitidine and an ion exchange resin to give a resin adsorbate which is substantially free of the bitter taste associated with ranitidine.

Other methods of taste-masking ranitidine are described in EP349103, EP459695, EP473431 and U.S. Pat. No. 5084278.

We have now found that the bitter taste of ranitidine may be masked by coating the drug substance with a suitable lipid.

One of the factors that governs the degree of taste masking obtained by lipid coating is the water solubility of the input drug substance. Thus, for forms of ranitidine which are only poorly soluble in water (e.g. less soluble salts of rantidine), the bitter taste associated with ranitidine may be satisfactorily masked by simple lipid coating of the drug substance. In the case of forms of ranitidine which are soluble in water to an appreciable extent (e.g. ranitidine base and certain of its salts), the degree of taste masking achieved by simple lipid coating of the drug substance may not be entirely satisfactory, particularly if the product is to be formulated in an aqueous medium or the product comes into contact with the wet environment of the mouth. We have found that the degree of taste masking achieved by coating the drug substance with a suitable lipid, especially when the ranitidine is in a form having an appreciable solubility in water, can be significantly enhanced if the drug substance is incorporated into a core prior to being coated with the lipid.

The resulting lipid coated particles, containing an inner core if required, are substantially insoluble in water but break down on contact with gastrointestinal fluid, such that the bitter taste associated with ranitidine is masked on oral administration, with subsequent release of the drug substance, by dispersion or dissolution, in the gastrointestinal tract.

Thus according to one aspect the present invention provides a composition which is substantially free of the bitter taste associated with ranitidine and comprises a) a dispersion of lipid coated particles of ranitidine or a physiologically acceptable salt thereof in a non-aqueous vehicle b) particles comprising ranitidine or a physiologically acceptable salt thereof incorporated into a core and coated with a lipid coating c) lipid coated particles of a form of ranitidine which is poorly soluble in water.

According to a further aspect, the present invention provides a composition for oral administration, which is substantially free of the bitter taste associated with ranitidine and comprises a dispersion of lipid coated particles of ranitidine or a physiologically acceptable salt thereof in a non-aqueous vehicle.

According to a yet further aspect, the invention provides a method of masking the bitter taste associated with ranitidine which comprises coating ranitidine or a physiologically acceptable salt thereof with a suitable lipid, and incorporating the lipid coated particles into a non-aqueous composition.

According to a yet further aspect the present invention provides particles for oral administration, comprising ranitidine or a physiologically acceptable salt thereof, optionally incorporated into a core, coated with a coating of a lipid, which particles are substantially free of the bitter taste associated with ranitidine.

According to a further aspect, the invention provides a method of masking the bitter taste of ranitidine which comprises coating ranitidine or a physiologically acceptable salt thereof, optionally incorporated into a core, with a suitable lipid.

Ranitidine may be employed according to the invention in the form of either its free base or a physiologically acceptable salt. Such salts include salts with inorganic or organic acids such as the hydrochloride, hydrobromide, sulphate, acetate, maleate, succinate, citrate, tartrate, fumarate and ascorbate salts. A particularly preferred salt of ranitidine is the hydrochloride.

Suitable lipids for the outer coating include fatty acids or monohydric alcohols thereof, fixed oils, fats, waxes, sterols, phospholipids and glycolipids either singly or in mixture. The lipid may, for example, be a high molecular weight ($C_{10}$–$C_{30}$) straight chain saturated or unsaturated aliphatic acid, such as palmitic or stearic acid; a mono- di- or tri- high molecular weight ($C_{10}$–$C_{30}$) aliphatic acid ester of glycerol, such as glyceryl tripalmitate, glyceryl tristearate or a mixed acid ester triglyceride; partially hydrogenated vegetable or animal oils such as hardened palm oil or hardened edible tallow; high molecular weight ($C_{10}$–$C_{30}$) straight chain aliphatic alcohols such as stearyl alcohol or cetyl alcohol; microcrystalline waxes consisting of straight-chain, branched-chain or cyclic hydrocarbons with average molecular weight 580 to 900; or a mixture thereof. Mixtures of lipids may also be used, including mixtures of glyceryl esters of high molecular weight aliphatic acids such as mixtures involving glyceryl trilaurate, glyceryl tristearate, glyceryl tripalmitate and/or mixed acid ester triglycerides;

mixtures of high molecular weight aliphatic acids such as mixtures of palmitic acid and stearic acid; mixtures of partially hydrogenated vegetable or animal oils and glyceryl esters such as hardened palm oil and glyceryl tripalmitate and mixtures of glyceryl esters with microcrystalline waxes such as glyceryl tripalmitate and microcrystalline wax. A particularly preferred lipid mixture is glyceryl tristearate in admixture with glyceryl trilaurate in a ratio in the range 9:1 to 1:4, more preferably 4:1 to 1:1, and in particular 3:1, by weight. The most preferred lipid is glyceryl tripalmitate of high purity having a low iodine value (preferably less than 1.0) and a low acid value (preferably less than 0.5).

The lipid coated particles of the invention will generally have a diameter of less that 1000 microns, preferably less than 500 microns, and more preferably less than 200 microns. Coated particles with a diameter in the range of 1–200 microns e.g. 20–150 microns are preferred. Control of the particle size is necessary to ensure that the subsequently formulated product does not produce a "gritty" feel in the mouth and particles having a diameter of less than about 150 microns are preferred in this respect.

The lipid coated particles of the invention may conveniently be prepared by atomising a dispersion of ranitidine or a physiologically acceptable salt thereof, or a dispersion of core particles containing the ranitidine or ranitidine salt, as appropriate, in a molten lipid, and cooling the resultant particles, and such a process constitutes a further feature of the invention. Atomising techniques which may be used include the use of conventional atomisers such as rotary atomisers, pressure nozzles, pneumatic nozzles and sonic nozzles. The use of a two-fluid pneumatic nozzle atomiser fitted in a standard spray drying/chilling apparatus is particularly convenient.

In the atomisation process using a pneumatic two-fluid nozzle atomiser, the molten lipid dispersion will generally be supplied to the atomiser head at a temperature in the range of 60° to 90° C., preferably 70° to 80° C., the precise temperature depending on the particular lipid used. The atomising gas supplied to the nozzle may be air or an inert gas such as nitrogen. The temperature of the gas will generally be within the range 70° to 100° C., preferably 75° to 85° C. with the precise temperature dependant upon the particular lipid material being used. It has been found that, in the coating process, the temperature at which the molten lipid dispersion is maintained is preferably in the range of 10° to 20° C. above the melting point of the lipid. The atomising pressure is desirably controlled in order to produce particles of a preferred size.

The molten dispersion may be prepared by dispersing the ranitidine or ranitidine salt, or core particles containing the ranitidine or ranitidine salt, as appropriate, in the molten lipid or mixture of lipids using conventional techniques. When the input drug substance has not been incorporated into cores, a high shear mixer may be used. When the input drug substance has been incorporated into cores prior to lipid coating, a low shear mixer should be used, to avoid disruption of the cores. In general, the lipid or lipid mixture used for the outer coating should have a melting point within the range of 30° to 100° C., preferably 40° to 85° C., and the temperature of the molten lipid will be 10° to 20° C. above its melting point. However, when overcoating cores which have been prepared by coating the input drug substance with a lipid or wax having a melting point which is higher than that of the outer lipid coating (as described hereinafter), the lipid or lipid mixture used for the outer coating preferably has a melting point of 40° to 60° C., and care must be taken not to allow the temperature of the mixture to rise above 10° C. below the melting point of the lipid or wax used to form the core.

The ranitidine content of the lipid coated particles may be, for example, in the range of 1 to 80%, preferably 10 to 70%, more preferably 15 to 50% on a weight-to-weight (w/w) basis, the ranitidine being in the form of the free base or a physiologically acceptable salt, most preferably in the form of ranitidine hydrochloride.

When the ranitidine is in a form which is soluble in water to an appreciable extent (e.g. in the form of ranitidine hydrochloride), such that it is necessary to incorporate the drug substance into inner cores prior to lipid coating, the final ranitidine content of the lipid coated particles will depend upon the input level of ranitidine in the core particles. When lipid coating cores containing the ranitidine or ranitidine salt, the cores may be dispersed in the molten lipid in an amount within the range of for example 1 to 80% by weight, preferably 20 to 70% by weight, and more preferably 30 to 60% by weight. The lipid provides the remainder of the weight of the molten dispersion.

When it is necessary to incorporate the drug substance into inner cores, the cores for subsequent lipid coating, which constitute a further aspect of the invention, comprise a dispersion of the ranitidine or a physiologically acceptable salt thereof (e.g. ranitidine hydrochloride) in either a polymeric binder, or a lipid or wax having a melting point which is higher than that of the outer lipid coating. The cores are preferably spherical in shape and ideally have a particle size approaching that desired for the final lipid coated product. This allows the application of a discrete overcoat of lipid or mixture of lipids to each drug particle thereby fully encapsulating the drug core and satisfactorily masking the taste of ranitidine.

Suitable polymeric binders for use in the drug cores include alkylcelluloses such as methylcellulose, ethylcellulose, propylcellulose; hydroxyalkylcelluloses (e.g. hydroxypropylcellulose or hydroxypropylmethylcellulose) and other cellulose based polymers (e.g. hydroxypropyl methylcellulose phthalate); polyvinylpyrrolidone; and polymer systems based on methacrylic acid or other acrylate polymers. Ethylcellulose is particularly preferred.

Cores comprising ranitidine or a physiologically acceptable salt thereof and a polymeric binder may be prepared by spray drying a suspension of the drug substance dispersed in a solution of the polymer in a suitable solvent. A suitable solvent is one in which the polymer is soluble, but the ranitidine or ranitidine salt is essentially insoluble. Particularly suitable solvents include a mixture of dichloromethane and ethanol.

The ratio of ranitidine to polymer in the suspension (the ranitidine being in the form of its free base or a physiologically acceptable salt) may be in the range 5:95 to 95:5, preferably 30:70 to 90:10, and more preferably 60:40 to 80:20, on a weight-to-weight (w/w) basis. The suspension or solution to be spray dried should contain 5 to 80% w/w solids (i.e. ranitidine or ranitidine salt together with polymer) preferably 10 to 60% w/w and more preferably 20 to 40% w/w. A particularly preferred suspension for spray drying contains 20% w/w ranitidine hydrochloride suspended in a solution of 10% w/w ethylcellulose and 3% w/w ethanol in dichloromethane.

The suspension may be spray dried using a conventional spray drier. Atomisation of the suspension may be achieved using either a rotary atomiser, pressure nozzle, pneumatic nozzle or sonic nozzle. The use of a two fluid external mixing pneumatic nozzle is particularly convenient. In the spray drying process the inlet gas fed into the spray dryer is heated to a temperature sufficient to remove the solvent from the droplets of atomised suspension or solution to produce spherical particles of the drug substance and the chosen polymer. For example, with a dichloromethane solvent system the temperature of the gas entering the chamber is preferably in the range 50° to 150° C., preferably 70° C. to 120° C. and more preferably 80° C. to 100° C. In addition to controlling the temperature of the chamber gas in the spray drying process it is necessary to control the feed rate and atomisation conditions for the suspension or solution to produce particles of the required shape and size. The preferred shape of the particles so formed is spherical. The presence of irregular shaped particles reduces the effectiveness of subsequent overcoating procedures in masking the bitter taste of the drug. The size of the particles is also important. The particles preferably have a diameter of less than 200 microns, more preferably in the range 5 to 100 microns.

In order to obtain lipid coated particles, or core particles for subsequent lipid coating, of the required size, it is necessary to reduce the particle size of the input drug substance. This may be achieved using several techniques including fluid energy milling, hammer milling, pin milling and ball milling. The process of pin milling is preferred and may be used, for example, to reduce the particle size of ranitidine hydrochloride to less than 150 microns and preferably less than 100 microns. Alternatively the particle size may be reduced sufficiently during the spray chilling procedure by high shear mixing of the molten mixture following dispersion of the input drug substance in the molten lipid(s). This may be achieved, for example, using a Silverson mixer fitted with a high shear square hole screen.

Where the cores for subsequent lipid coating comprise a dispersion of ranitidine or a physiologically acceptable salt thereof in a lipid or wax having a melting point which is higher than that of the outer lipid coating, the lipid or wax used for the core may have a melting point of for example 80° C. or above, in order to prevent melting of the core during the subsequent lipid coating process. Suitable lipids or waxes used in forming the cores include triglycerides of long chain saturated fatty acids; long chain fatty acids; long chain fatty alcohols; microcrystalline waxes consisting of straight-chain, branched-chain and cyclic hydrocarbons; or mixtures of these, suitably chosen (having regard to melting point) from the types of lipids listed previously. In the case of ranitidine hydrochloride, for example, the naturally occurring wax, carnauba wax, is particularly preferred.

The dispersion may be formed by melting the lipid or wax and raising the temperature of the molten material to 20° C. to 30° C. above its melting point. To this is then added the ranitidine or ranitidine salt of a suitably low particle size, to give a solids content in the molten dispersion of 20 to 80% w/w, preferably 40 to 70% w/w and more preferably 50 to 70% w/w. A particularly preferred dispersion comprises 60% w/w ranitidine hydrochloride in carnauba wax.

The molten dispersion is then spray chilled as described previously using atomising air heated to a temperature approximately 20° to 30° C. above the melting point of the lipid or wax. Generally there is no need to chill the inlet air in the spray chiller. The product is collected as a free flowing powder using either a cyclone separator or bag filter. The particles are spherical in shape and have a particle size preferably less than 200 microns and more preferably in the range 5 to 100 microns.

Particularly preferred lipid coated particles according to the invention comprise cores consisting of ranitidine hydrochloride in an ethylcellulose matrix overcoated with glyceryl tripalmitate.

A preferred lipid coated product for suspension in a non-aqueous vehicle comprises particles of ranitidine hydrochloride coated with a mixture of glyceryl tristearate and glyceryl trilaurate or, more preferably, with glyceryl tripalmitate.

The lipid coated particles of the invention may be incorporated into a pharmaceutical composition for oral administration, using one or more physiologically acceptable carriers or excipients.

The amount of ranitidine, preferably in the form of a physiologically acceptable salt, particularly ranitidine hydrochloride, in the oral formulation is preferably in the range of 10 to 800 mg per dosage unit, e.g. 20 to 600 mg, more preferably 25 to 300 mg, such as 25, 75, 125 or 150 mg, expressed as the weight of free base.

The unit dose may be administered up to, for example, 6 times a day depending upon the unit dose used, the nature and severity of the conditions being treated, and the age and weight of the patient. Thus, for example, in the treatment of minor conditions where there is an advantage in lowering gastric acidity such as, for example, acid indigestion, overindulgence of food or drink, acid stomach, sour stomach, heartburn, such as episodic heartburn, nocturnal heartburn, and meal-induced heartburn, gastritis and dyspepsia, lower and more frequent doses of ranitidine may be used, for example doses in the range of 10–150 mg, e.g. 25–75 mg ranitidine expressed as the weight of free base, administered up to 6 times a day as and when required. For more serious conditions such as duodenal and gastric ulceration, reflux oesophagitis and Zollinger-Ellison syndrome, higher and less frequent doses of ranitidine will be employed, for example 75–600 mg, e.g. 150 mg unit doses administered one to four, preferably once or twice, daily.

The compositions according to the invention may for example take the form of tablets, capsules, granules, powders, tablets or lozenges for buccal administration, or liquid preparations such as suspensions. Chewable or suckable tablets, granules, and suspensions represent particularly preferred dosage forms. Granules may be ingested directly, taken with for example a draught of water, or dispersed in water (if the ranitidine is in a form which is poorly soluble in water) or other suitable vehicle prior to administration. The suspensions may be non-aqueous and, in the case of forms of ranitidine which are poorly soluble in water, the lipid coated material may also be formulated as an aqueous suspension.

The pharmaceutical compositions according to the invention, comprising a dispersion of lipid coated particles of ranitidine or a physiologically acceptable salt thereof in a non-aqueous vehicle, formulated for oral administration, may be presented in the form of, for example, non-aqueous suspensions, chewable soft gelatin capsules, or chewable tablets. Non-aqueous suspensions are preferred.

The compositions may be formulated using conventional pharmaceutically acceptable carriers or excipients.

Thus for example granules may be prepared by granulating the lipid coated particles with a binding agent using well known pharmaceutical granulation techniques, more particularly fluidised bed granulation. Suitable binding agents include an alkylcellulose or polyvinylpyrrolidone, more preferably hydroxypropylmethylcellulose. It may also be beneficial to add a small amount of a pharmaceutically acceptable surface active agent (e.g. sodium lauryl sulphate) to the granulating fluid to aid the wetting of the particles. The granules are dried using conventional pharmaceutical drying techniques taking care not to allow the temperature of the granules to rise to within about 10° C. of the melting point of the outer lipid coating.

Tablets of the lipid coated particles may be obtained by compressing the granules. Alternatively a dry mix of the various excipients used for granule formation could be compressed together with suitable binding agents e.g. polyvinylpyrrolidone. Chewable tablets may be prepared incorporating the lipid coated particles with a suitable chewable base such as sucrose, glucose, lactose, maltose or a mixture thereof, preferably sucrose, according to conventional procedures. Cast chewable tablets may be prepared by incorporating the lipid coated particles into low melting point fatty bases. The chosen fatty base should have a melting point that is sufficiently high to give a solid tablet at room temperature and preferably at temperatures up to 30° C. but not too high so as to cause melting of the outer lipid coating during processing or to reduce the bioavailability of the drug. Suitable bases are for example macrogols, fatty acids, mono- di- and tri-glycerides, alkanes, and fatty alcohols either alone or in admixture. In the case of ranitidine hydrochloride, for example, particularly preferred fatty bases are suppository bases which melt at about 37° C. and are pharmaceutically acceptable e.g. hard fat and theobroma oil.

Suitable non-aqueous vehicles for use in the compositions according to the invention, particularly non-aqueous suspensions and chewable soft gelatin capsules, include fractionated coconut oil fractionated coconut oil cross-linked with an organic acid such as succinic acid, arachis oil, sesame oil, soya oil and other animal vegetable or synthetic oils suitable for oral administration, used either singly or in admixture.

Aqueous suspensions may be obtained by dispersing the lipid coated particles in an aqueous vehicle. Suitable vehicles include sucrose syrup; hydrogenated sucrose syrup; sorbitol solution and concentrated solutions of other sugars; aqueous solutions thickened with cellulose based polymers such as hydroxypropylmethyl cellulose, methylcellulose or microcrystalline cellulose in suspension; aqueous solutions thickened with polysaccharides such as starch; aqueous solutions thickened with polyacrylates such as carbopol; and aqueous solutions thickened with colloidal dispersing agents such as magnesium aluminium silicate. Various pharmaceutically acceptable excipients such as preservatives and buffer salts may also be included. In addition, surface active agents may be added to aid wetting of the lipid coated particles.

The various preparations may also contain bulk sweeteners (e.g. sucrose), intense sweeteners (e.g. sodium saccharin or aspartame) and/or flavouring agents as appropriate.

The compositions according to the invention may, if desired, be administered in combination with one or more other therapeutic agents, for example the compositions may also contain a suitable antacid such as calcium carbonate.

The following Preparations 1 and 2 illustrate the preparation of core particles according to the invention containing ranitidine hydrochloride. Ranitidine in the form of its free base or a physiologically acceptable salt may be incorporated into cores in a similar manner.

PREPARATION 1

Ethylcellulose (250 g) was dissolved in dichloromethane (1000 g) containing ethanol (72 g). To this was added ranitidine hydrochloride (500 g) of a low particle size (less than 100 microns) dispersed in dichloromethane (780 g). The suspension was mixed under high shear until homogeneous, and then pumped into a spray drier at a flow rate of approximately 260 g/minute and atomised using an external mixing two-fluid pneumatic nozzle (dimensions 80/150/180 thousandths of an inch) with an atomising air pressure of 60 psi. The temperature of inlet air into the chamber was 85° C. The product was collected using a cyclone separator and was composed of mostly spherical particles in the size range 1 to 300 microns with most of the material having a particle diameter of less than 200 microns.

PREPARATION 2

Carnauba wax (prime yellow grade) (400 g) was melted and heated to 100° C. To this was added milled ranitidine hydrochloride (600 g) of a low particle size (less than 100 microns) and this was dispersed by mixing with a paddle. The molten dispersion at 100° C. was spray chilled at a rate of approximately 500g/minute using an internal mixing two-fluid pneumatic nozzle fed with atomising air at a pressure of 60 psi and a temperature of 100° C. The solidified product was collected and found to comprise spherical particles up to 300 microns in diameter. Particles greater than 200 microns were removed by sieving.

The following Examples 1, 2 and 3 illustrate the preparation of lipid coated particles according to the invention, in which cores as described in Preparations 1 and 2 are overcoated with lipid.

EXAMPLE 1

Glyceryl tristearate (525 g) and glyceryl trilaurate (175 g) were melted together and raised to a temperature of 75° C. To the molten lipids was added spray dried ranitidine hydrochloride-ethylcellulose core particles (300 g) containing 66.6% w/w ranitidine hydrochloride. The molten dispersion was mixed to give a homogeneous suspension and pumped into a spray dryer/chiller apparatus (chamber height 2 m) at a rate of approximately 500 g/minute and atomised using an external mixing two-fluid pneumatic nozzle (with nozzle dimensions 100/150/180 thousandths of an inch) and atomising air at a temperature approximately 20° C. above the melting point of the lipid mixture and an atomising pressure of 60 psi. The product was chilled using air fed into the spray chamber at a temperature of 14° C. and the solid product collected in a cyclone separator. The product had a particle size range of 1–300 microns with the majority of the particles with diameters less than 200 microns. The final ranitidine hydrochloride content was 20% w/w and the material was substantially tasteless.

EXAMPLE 2

Glyceryl tripalmitate (200 g) was melted and raised to a temperature of 72° C. To this was added ranitidine hydrochloride- carnauba wax core particles (100 g) containing 60% w/w ranitidine hydrochloride. The core particles were mixed in using a paddle to give a homogeneous suspension and the temperature of the dispersion maintained at 72° C. The molten dispersion was then spray chilled at a rate of about 500 g/minute as detailed above using an internal mixing two-fluid pneumatic nozzle with an atomising air pressure of 60 psi and temperature of 73° C. The resulting particles had a particle size range of about 1 to 300 microns with the majority of the particles having diameters less than 200 microns. The final ranitidine hydrochloride content was 20% w/w and the material was substantially tasteless.

EXAMPLE 3

Glyceryl tripalmitate (350 g) was melted and raised to a temperature of 75° C. To the molten lipid was added spray dried ranitidine hydrochlorideethylcellulose core particles (150 g) containing 66.6% w/w ranitidine hydrochloride. The molten dispersion was mixed to give a homogeneous suspension and pumped into a spray dryer/chiller apparatus (chamber height 2 m) at a rate of approximately 500 g/minute and atomised using an external mixing two-fluid pneumatic nozzle (with nozzle dimensions 100/150/180 thousandths of an inch) and atomising air at a temperature approximately 20° C. above the melting point of the lipid mixture and an atomising pressure of 60 psi. The product was chilled using air fed into the spray chamber at a temperature of 14° C. and the solid product collected in a cyclone separator. The product had a particle size range of 1–300 microns with the majority of the particles with diameters less than 200 microns. The final ranitidine hydrochloride content was 20% w/w and the material was substantially tasteless.

The following Examples 4 and 5 illustrate the preparation of lipid coated particles of ranitidine hydrochloride. Other physiologically acceptable salts, or ranitidine in the form of its free base, may be lipid coated in a similar manner, using suitably chosen lipid(s).

EXAMPLE 4

Glyceryl tripalmitate (1200 g) was melted and raised to a temperature of 75° C. To this was added ranitidine hydrochloride (300 g). The molten dispersion was mixed to give a homogeneous suspension and pumped to a spray drier/chiller apparatus (chamber height 2 m) at a rate of approximately 500 g/minute. The mixture was atomised using an external mixing two-fluid pneumatic nozzle (with nozzle dimensions 80/150/180 thousandths of an inch) and atomising air at a temperature approximately 30° C. above the melting point of the lipid and an atomising pressure of 50 psi. The atomised droplets were chilled using air fed into the spray chamber at a temperature of 10° C. and the solid product collected in a cyclone separator. The product comprised spherical particles with a median particle size of 120 microns.

EXAMPLE 5

Glyceryl tristearate (900 g) and glyceryl trilaurate (300 g) were melted together and raised to a temperature of 75° C. To this was added ranitidine hydrochloride (300 g). The molten dispersion was subjected to high shear mixing using a Silverson high shear mixer for 10 minutes to reduce the ranitidine hydrochloride particle size. This mixture was spray chilled as described in Example 4, to give a product having a similar particle size and shape.

The following Examples A, B, C and D illustrate pharmaceutical compositions according to the invention in which the lipid coated particles are in particular as described in Examples 2 and 3 above. Other types of lipid coated particles according to the invention, containing an inner core into which is incorporated ranitidine free base or another water-soluble physiologically acceptable salt thereof may be formulated in a similar manner.

EXAMPLE A

Flavored Granules

| (i) Lipid coated ranitidine hydrochloride * | 75 g |
|---|---|
| Xylitol (powdered) | 120 g |
| Flavour (peppermint) | 2 g |
| Granulating fluid ** | 30 ml |

* Contains 20% w/w ranitidine hydrochloride as a ranitidine hydrochloride - carnauba wax core overcoated with glyceryl palmitate.
** 10% w/v solution of hydroxypropylmethyl cellulose (3 centipoise grade) in ethanol (85%)/water (15%) mixture.

The solids were mixed and fluidised in a fluid bed granulator. The temperature of the bed was raised to 40° C. and the granulating fluid sprayed onto the bed. The resulting granules were dried and screened (1.0 mm sieve). Each 2.24 g of granules contained 168 mg ranitidine hydrochloride (equivalent to 150 mg ranitidine free base) and may be taken dry or first dispersed in water.

| (ii) Lipid coated ranitidine hydrochloride* | 75 g |
|---|---|
| Xylitol (powdered) | 120 g |
| Flavour (peppermint) | 2 g |
| Granulating fluid** | 30 ml |

*Contains 20% w/w ranitidine hydrochloride as a ranitidine hydrochloride-ethylcellulose core overcoated with glyceryl tripalmitate.
**10% w/w solution of hydroxypropylmethyl cellulose (3 centipoise grade) in ethanol (85%)/water (15%) mixture.

The granules were formed as described in Example A (i).

EXAMPLE B

Compressed Chewable Tablets

The granules produced in Examples A(i) and A(ii) were mixed with 0.5% w/w magnesium stearate and then compressed using a conventional pharmaceutical tablet press. Each tablet weighed 2.24 g and contained 168 mg ranitidine hydrochloride (equivalent to 150 mg ranitidine free base).

EXAMPLE C

Cast Chewable Tablet

| per tablet | |
|---|---|
| Lipid coated ranitidine hydrochloride * | 0.84 g |
| Witepsol H15 ** | 1.8 g |
| Theobroma oil BP | 0.36 g |
| Aspartame | 0.01 g |
| Flavour | 0.005 g |

* Contains 20% w/w ranitidine hydrochloride as a ranitidine hydrochloride-ethylcellulose core overcoated with glyceryl tripalmitate.
** Triglyceride suppository base manufactured by Dynamit Nobel.

The Witepsol H15 and theobroma oil were melted together and heated to 36° C. The solids were incorporated and the molten mixture cast into tablet shaped moulds. After solidification the tablets were removed. Each tablet weighed about 3 g and contained 168 g ranitidine hydrochloride.

EXAMPLE D

Non-Aqueous Suspension

| Lipid coated ranitidine hydrochloride * | 16.8 g |
|---|---|
| Xylitol (powdered) | 18.0 g |
| Aspartame | 2.0 g |
| Flavour | q.s. |
| Fractionated coconut oil | to 100 ml |

* Contains 20% w/w ranitidine hydrochloride as a ranitidine hydrochloride-ethylcellulose core overcoated with glyceryl tripalmitate.

The lipid coated ranitidine hydrochloride, xylitol, aspartame and flavour were added to the bulk of the fractionated coconut oil and mixed using a Silverson mixer fitted with a low shear head. The suspension was then made up to volume with fractionated coconut oil and mixed to give a homogeneous suspension. The dose of ranitidine hydrochloride was 168 mg per 5 ml.

The following Examples E, F and G illustrate non-aqueous pharmaceutical compositions according to the invention, in which the lipid coated material is in particular as described in the above Examples 4 and 5. Other lipid coated materials formed by coating ranitidine or a physiologically acceptable salt thereof with other types of lipid(s) may be formulated in a similar manner.

EXAMPLE E

Non-aqueous suspension (i) For 100 ml

| | |
|---|---|
| Glyceryl tripalmitate coated ranitidine hydrochloride (containing 20% w/w ranitidine hydrochloride) | 16.8 g |
| Aspartame | 2.0 g |
| Mannitol (powdered) | 18.0 g |
| Flavour | q.s. |
| Fractionated coconut oil | to 100 ml |

The lipid coated ranitidine hydrochloride, mannitol, aspartame and flavour were added to the bulk of the fractionated coconut oil and mixed using a Silverson mixer fitted with a low shear head. The suspension was then made up to volume with fractionated coconut oil and mixed to give a homogeneous suspension. The dose of ranitidine hydrochloride was 168 mg per 5 ml (equivalent to 150 mg free base).

(ii) For 100 ml

| | |
|---|---|
| Ranitidine hydrochloride (20% w/w) coated with a 3:1 mixture of glyceryl tristerate and glyceryl trilaurate | 16.8 g |
| Xylitol (powdered) | 18.0 g |
| Aspartame | 1.5 g |
| Flavour | q.s. |
| Fractionated coconut oil | to 100 ml |

The suspension was prepared by the method described in Example E(i).

EXAMPLE F

Chewable soft gelatin capsule per capsule

| | |
|---|---|
| Ranitidine hydrochloride (30% w/w) coated with glyceryl tripalmitate | 0.56 g |
| Aspartame | 0.03 g |
| Flavour | q.s. |
| Fractionated coconut oil | 0.7 g |

The ingredients are mixed, and the mixture filled into soft gelatin capsules.

EXAMPLE G

Cast chewable tablet per tablet

| | | | |
|---|---|---|---|
| Glyceryl tripalmitate coated ranitidine hydrochloride (containing 20% w/w ranitidine hydrochloride) | 0.84 g | | |
| Witepsol H15* | 1.8 g | Theobroma oil BP | 0.36 g |
| Aspartame | 0.01 g | | |
| Flavour | 0.05 g | | |

*Triglyceride suppository base manufactured by Dynamit Nobel.

The Witepsol H15 and theobroma oil are melted together and heated to 36° C. The solids are incorporated and the molten mixture cast into tablet shaped moulds. After solidification the tablets are removed. Each tablet weighs about 3 g and contains 168 g ranitidine hydrochloride (equivalent to 150 mg free base).

We claim:

1. A composition which is substantially free of the bitter taste associated with ranitidine and comprises particles having a core and a lipid coating around the core wherein the core comprises a dispersion of ranitidine, or a physiologically acceptable salt thereof, in a binder selected from the group consisting of polyvinylpyrrolidone, acrylate polymers and cellulose-based polymers and wherein the lipid coating comprises lipids selected from the group consisting of fatty acids or monohydric alcohols thereof, fixed oils, fats, sterols, phospholipids, glycolipids and mixtures thereof.

2. A composition as claimed in claim 1 wherein the lipid is mono-, di- or tri-$C_{10}$–$C_{30}$ aliphatic ester of glycerol or a mixture thereof.

3. A composition as claimed in claim 2 wherein the lipid mixture comprises glyceryl tristearate in admixture with glyceryl trilaurate in a ratio in the range 9:1 to 1:4.

4. A composition as claimed in claim 1 wherein the particles have diameters in the range of 1–200 microns.

5. A composition as claimed in claim 1 wherein the ranitidine content of the particles is in the range of 10 to 70% w/w, the ranitidine being in the form of the free base or a physiologically acceptable salt thereof.

6. A composition as claimed in claim 1 containing ranitidine hydrochloride.

7. A process for the preparation of a composition as claimed in claim 1 which comprises dispersing the cores in a molten lipid, atomizing the dispersion and cooling and collecting the coated cores thereby obtained.

8. A pharmaceutical composition for oral administration comprising a composition as claimed in claim 1, together with one or more physiologically acceptable carriers or excipients.

9. A pharmaceutical composition for oral administration comprising a composition as prepared by a process as claimed in claim 7, together with one or more physiologically acceptable carriers or excipients.

10. A pharmaceutical composition as claimed in claim 8 in the form of chewable or suckable tablets, chewable soft gelatin capsules, suspensions or granules.

11. A pharmaceutical composition as claimed in claim 9 in the form of chewable or suckable tablets, chewable soft gelatin capsules, suspensions or granules.

12. A pharmaceutical composition as claimed in claim 8 containing 10 to 800 mg ranitidine per dosage unit, expressed as the weight of free base.

13. A pharmaceutical composition as claimed in claim 9 containing 10 to 800 mg ranitidine per dosage unit, expressed as the weight of free base.

14. The composition of claim 1 wherein the binder has a melting point which is higher than that of the lipid coating.

15. The composition of claim 14 wherein the cellulose-based polymeric binder is an alkyl cellulose.

16. The composition of claim 1 wherein said composition is an aqueous composition.

17. The composition of claim 1 wherein the lipid coating comprises lipids selected from the group consisting of glyceryl tristearate, glyceryl trilaurate, glyceryl tripalmitate, triglyceride suppository base, theobroma oil, coconut oil and mixtures thereof.

* * * * *